US006891946B2

United States Patent
Kozic et al.

(10) Patent No.: US 6,891,946 B2
(45) Date of Patent: May 10, 2005

(54) AUTOMATED PHONE PRIORITIES

(75) Inventors: Dejan Kozic, Wadsworth, IL (US); Karl E. Meehan, Grayslake, IL (US)

(73) Assignee: Walgreen, Co., Deerfield, IL (US)

( * ) Notice: Subject to any disclaimer, the term of this patent is extended or adjusted under 35 U.S.C. 154(b) by 62 days.

(21) Appl. No.: 10/056,641

(22) Filed: Jan. 25, 2002

(65) Prior Publication Data

US 2003/0142810 A1 Jul. 31, 2003

(51) Int. Cl.$^7$ ............................................. H04M 3/00
(52) U.S. Cl. ............................ 379/265.12; 379/88.22; 370/352; 705/2; 705/3; 705/4; 705/5; 709/206
(58) Field of Search .................... 379/265.01–266.1, 379/88.22, 309, 67.1; 370/352, 356; 705/2–5; 704/9; 221/7, 9, 13; 709/206, 229

(56) References Cited

U.S. PATENT DOCUMENTS

| | | | |
|---|---|---|---|
| 5,703,943 A | | 12/1997 | Otto |
| 5,903,641 A | * | 5/1999 | Tonisson ............... 379/265.12 |
| 5,946,388 A | * | 8/1999 | Walker et al. ......... 379/266.01 |
| 6,088,429 A | * | 7/2000 | Garcia .................... 379/88.22 |
| 6,128,380 A | | 10/2000 | Shaffer et al. |
| 6,188,758 B1 | | 2/2001 | Christensen et al. |
| 6,192,122 B1 | | 2/2001 | Flockhart et al. |
| 6,198,812 B1 | | 3/2001 | Weber |
| 6,205,214 B1 | | 3/2001 | Culli et al. |
| 6,252,952 B1 | | 6/2001 | Kung et al. |
| 6,424,709 B1 | * | 7/2002 | Doyle et al. ............ 379/265.02 |
| 6,493,427 B1 | * | 12/2002 | Kobylevsky et al. ...... 379/67.1 |
| 2001/0040887 A1 | * | 11/2001 | Shtivelman et al. ........ 370/352 |

* cited by examiner

Primary Examiner—Fan Tsang
Assistant Examiner—Md Shafiul Alam Elahee
(74) Attorney, Agent, or Firm—Marshall, Gerstein & Borun LLP

(57) ABSTRACT

A method of automatically routing a telephone call in a pharmacy, comprising the steps of: activating a telephone when a pharmacy employee signs onto a workstation; identifying a position type for the pharmacy employee, wherein the position type is associated with a set of functions available to the pharmacy employee; assigning a phone priority to the pharmacy employee after the pharmacy employee signs onto the workstation; identifying a type of phone call associated with a caller; evaluating a set of resources available to handle the type of phone call; directing the caller to an available pharmacy employee having the position type preferred to handle the call type and having the highest phone priority; placing the caller in a hierarchical holding cue if no pharmacy employee having the position preferred to handle the call type is available until a pharmacy employee having the position type preferred to handle the call type becomes available; and deactivating the telephone when the pharmacy employee signs off of the workstation.

22 Claims, 6 Drawing Sheets

US 6,891,946 B2

AUTOMATED PHONE PRIORITIES

FIELD OF THE INVENTION

The present invention relates generally to a system for automatically routing telephone calls within a pharmacy to maximize customer service and internal workflow.

BACKGROUND OF THE INVENTION

Pharmacies have traditionally received telephone calls from patients, prescribers (physicians, nurses, physician assistants, etc.), insurers, and other parties. With the patients, the pharmacies receive calls from them for a variety of reasons. For example, the patients may call a pharmacy to request that a prescription be filled, to inquire if a prescription has been filled and is ready to be picked up, to request that a pharmacy employee call a prescriber's office, to inquire about a medication or an illness, or for a wide variety of additional reasons. The prescribers may also call a pharmacy for a wide variety of reasons, however the prescribers most commonly call the pharmacy to order a prescription for a patient. The call volume experienced by most pharmacies is very high in relation to the number of pharmacy employees staffed at any given time. Therefore, it is very important that the telephone calls are directed to the pharmacy employees in a manner that is as efficient as possible. This increases the overall satisfaction of the patients, prescribers, and other parties calling the pharmacy.

Many systems have been commercially developed to distribute a large number of calls to an organization's employees. However, these systems have primarily been directed to call center applications and do not take into account the specific needs of a pharmacy. Specifically, no systems to date have been developed that take into account the unique skill sets of pharmacists, technicians, and other staff members when distributing telephone calls to increase the overall workflow of a pharmacy as a whole.

BRIEF DESCRIPTION OF THE INVENTION

DETAILED DESCRIPTION OF VARIOUS EMBODIMENTS

Figure 1:
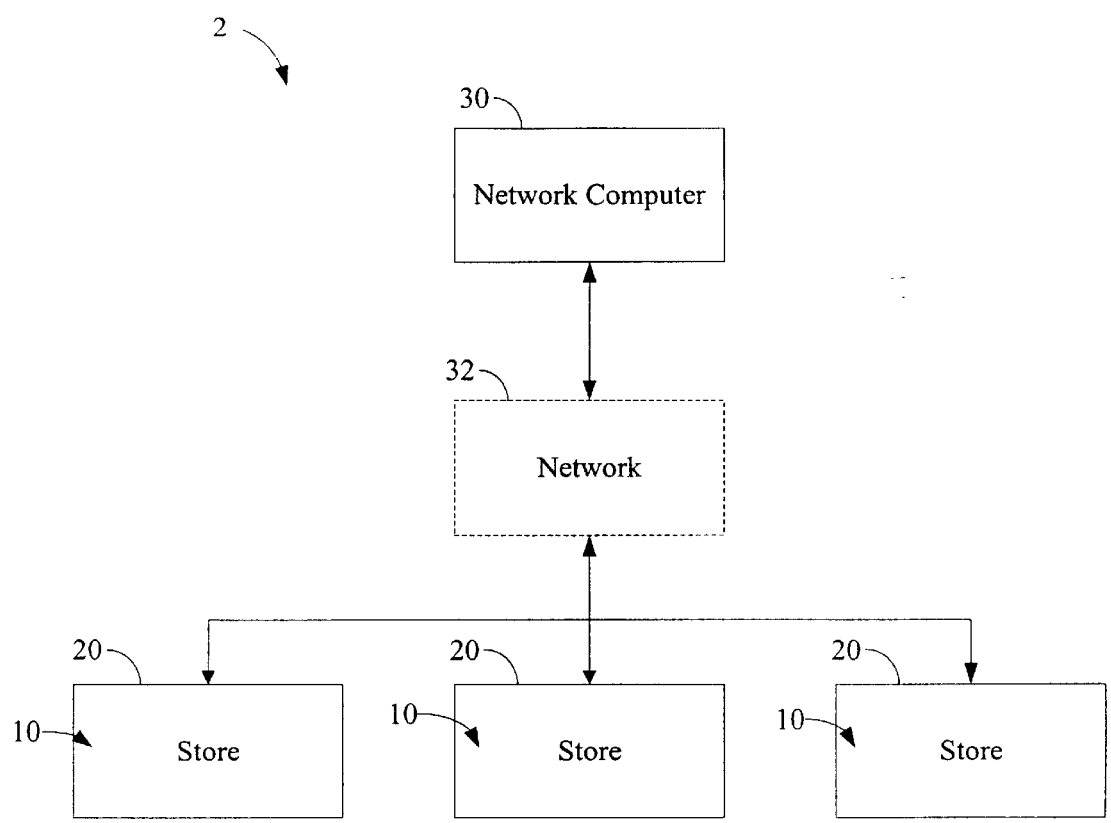
FIG. 1 is a block diagram of an embodiment of an intelligent network system in accordance with the invention.

FIG. 1 illustrates an embodiment of a pharmacy data network 2 in accordance with the invention. Referring to FIG. 1, the pharmacy data network 2 may include a first group of stores or facilities 20 operatively coupled to a network computer 30 via network data link 32. The plurality of stores 20 may be located in separate geographic locations from each other and may include an automatic telephone routing system 10. The stores 20 may be located in different areas of the same city, or they may be located in different states. The network 32 may be provided using a wide variety of techniques well know to those skilled in the art for the transfer of pharmacy data. For example, the network 32 may comprise dedicated access lines, plain, ordinary telephone lines, satellite links, combinations of these, etc. Additionally, the network 32 may include a plurality of network computers or server computers (not shown), each of which may be operatively interconnected. Where the network 32 comprises the Internet, data communication may take place over the communication link 32 via an Internet communication protocol.

The network computer 30 may be a server computer. It may be used to accumulate, analyze, and download data relating to the operation of the stores 20 and more particularly to the pharmacies within the stores 20. For example, the network computer 30 may continuously receive data from each of the stores 20 indicative of the prescriptions being requested and filled within the pharmacies that are located in the stores 20. This information may also be downloaded back to the other stores 20 via the network 32. The network computer 30 may include a database that may be utilized to store patient, prescriber, and prescription information.

Although the pharmacy data network 2 is shown to include one network computer 30 and three stores 20, it should be understood that different numbers of computers and stores may be utilized. For example, the network 32 may include a plurality of network computers 30 and hundreds or thousands of stores 20, all of which may be interconnected via the network 32. This configuration provides several advantageous, such as enabling near real time as well as periodic uploads and downloads of information. This provides for a primary backup of all the valuable patient and prescription information, thus enabling a patient to go into any one of the stores 20 and have a prescription filled via a central lookup.

Figure 2:
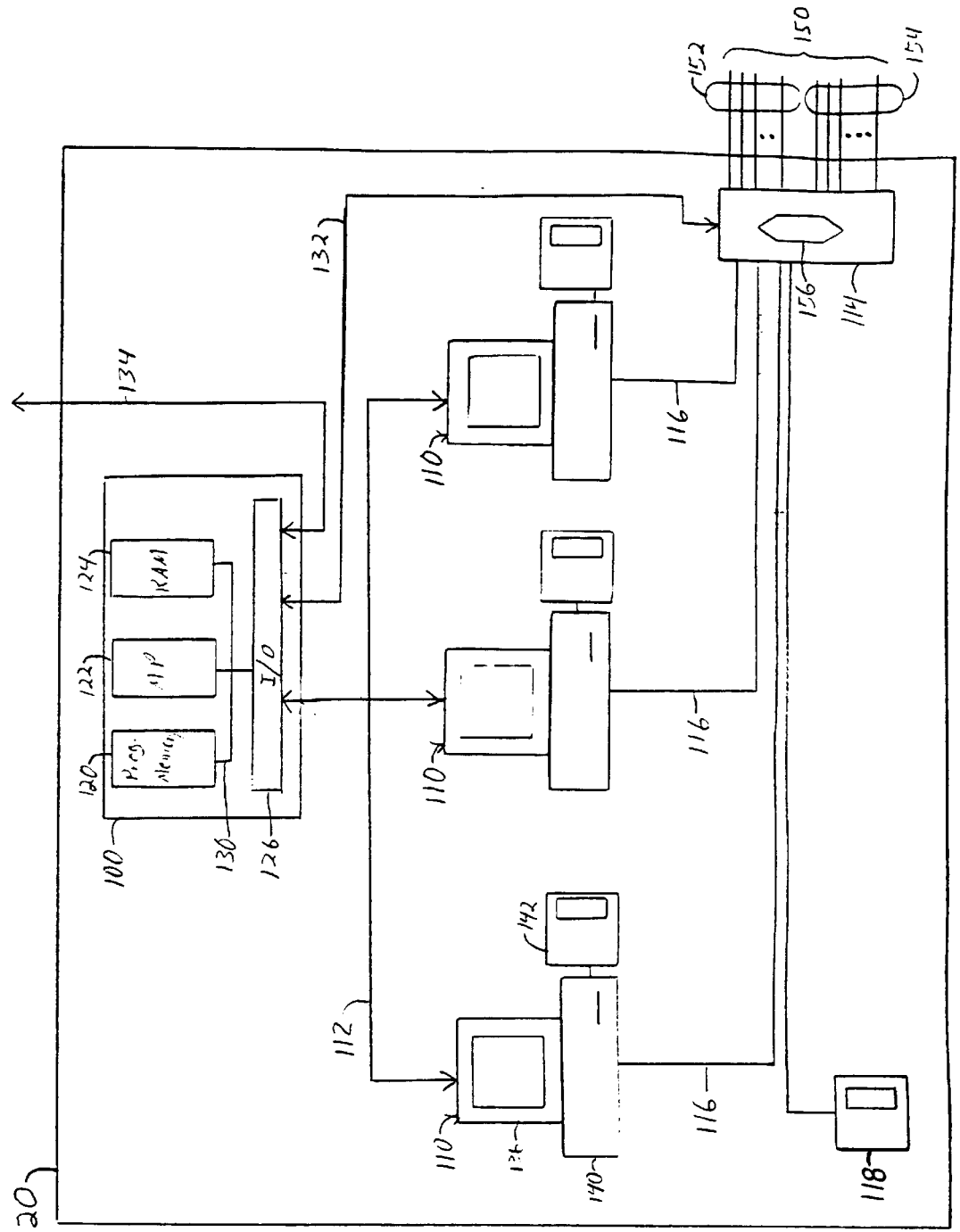
FIG. 2 is a schematic diagram of an embodiment of one of the facilities shown schematically in FIG. 1.

FIG. 2 is a schematic diagram of one possible embodiment of an automatic telephone routing system 10 located in one or more of the stores 20 from FIG. 1. Although the following description addresses the design of the stores 20, it should be understood that the design of one or more of the stores 20 may be different than the design of other stores 20. Also, each store 20 may have various different structures and methods of operation. It should also be understood that the embodiment shown in FIG. 2 illustrates some of the voice and data connections present in a pharmacy section of a store, however it does not illustrate all of the voice and data connections present in a typical store. For exemplary purposes, various designs of the stores are described below, but it should be understood that numerous other designs may be utilized.

The store 20 may have a controller 100 that is operatively connected to a plurality of work stations 110 via a network 112. The network 112 may be a wide area network (WAN), a local area network (LAN), or any other type of network known to those skilled in the art. The workstations 110 may also be operatively connected to a telephone switching mechanism 114, such as a private branch exchange (PBX), via links 116. The telephone switching mechanism 114 may also be connected to a stand alone telephone 118 that is not connected to a workstation 110.

The controller 100 may include a program memory 120, a microcontroller or a microprocessor (MP) 122, a random-access memory (RAM) 124, and an input/output (I/O) circuit 126, all of which may be interconnected via an address/data bus 130. It should be appreciated that although only one microprocessor 122 is shown, the controller 100 may include multiple microprocessors 122. Similarly, the memory of the controller 100 may include multiple RAMs 124 and multiple programs memories 120. Although the I/O circuit 126 is shown as a single block, it should be appreciated that the I/O circuit 126 may include a number of different types of I/O circuits. The RAM(s) 124 and programs memories 120 may be implemented as semiconductor memories, magnetically readable memories, and/or optically readable memories, for example. The controller 100 may also be operatively connected to the switching mechanism 114 via a link 132, which may or may not be part of the WAN 112. Additionally, the controller 100 may be operatively connected to the network computer 30 and the network computer's database via a data link 134 that is part of the network 32.

The workstations 110 may include a display 136, a controller 140, and a telephone 142. Each workstation 110 may be signed onto and occupied by a pharmacy employee to assist them in performing their duties. Pharmacy employees may sign onto a workstation 110 using any generically available technique, such as entering a user name and password. When a pharmacy employee signs onto a workstation 110, this information may be passed via the link 112 to the controller 100, so that the controller 100 will be able to identify which pharmacy employees are signed onto the system and which workstation 110 the employees are signed onto.

Still referring to FIG. 2, the store 20 may have a plurality of multiport telephone lines 150 that are utilized to connect the store 20 to a local exchange carrier (LEC). The telephone lines 150 may be connected to the telephone switching mechanism 114 and may be set up with the LEC so that they are divided into a first hunt group 152 and a second hunt group 154. The telephone lines in the first hunt group 152 may be designated to receive telephone calls from patients, prescribers, insurers, etc. and the telephone lines in the second hunt group 154 may be designated to receive telephone calls from customers wanting to reach other departments within the store, such as the camera department, the cosmetic department, the store manager, etc.

The first hunt group 152 may operate so that a single telephone number can be published and provided to all customers wanting to call into the pharmacy, wherein a plurality of customers may call the same telephone number and reach the pharmacy at the same time. For example, a first caller may call a pharmacy that is connected to the telephone switching mechanism 114 via the first line of the telephone lines 150 in the first hunt group 152. Then when a second caller calls the same published number, it may be connected to the switching mechanism 114 via a second line in the first hunt group 152. This will continue until all of the telephone lines in the first hunt group 152 are occupied by telephone calls. At that point additional callers may receive a busy signal when calling the published number. The telephone lines in the second hunt group 154 may operate in a similar manner. It should be noted that additional hunt groups may be added to connect additional telephone lines to the switching mechanism 114. Additionally, the first hunt group 152 and the second group 154 may be replaced by a single hunt group that would encompass all of the telephone lines 150.

The telephone switching mechanism 114 may include an automated attendant 156 that allows a caller an option to self direct once they have reached the switching mechanism 114. The automated attendant 156 may be programmed to respond to both tones corresponding to numbers pressed on the caller's telephone and to spoken numbers or voice commands by the callers. For example, the automated attendant 156 may be programmed to play a message requesting the caller to "press or say one if you are a patient, press or say 2 if you are a physician or a physician's assistant." The automated attendant 156 may assist the caller in reaching the appropriate pharmacy employee even if the caller dialed the wrong published number.

The caller's response to the automated attendant 156 may be used to identify the type of phone call associated with the caller. In other words, the caller's response may be used to identify whether the telephone call is from a prescriber, a patient, or other party. The information representing the type of phone call associated with the caller may then be sent to the controller 100 via the link 132. The controller 100 may then evaluate a set of resources (pharmacy employees or staff) that are available to handle the type of phone call. The controller 100 may then command the switching mechanism 114 to connect the caller to the available pharmacy employee having the position type or set of skills preferred to handle the call type in a way that maximizes the pharmacy's internal efficiency as well as maximizing customer service.

Overall Operation of the Automatic Telephone Routing System

One manner in which one or more of the stores 20 may operate is described below in connection with a number of flow charts which represent a number of portions or routines of one or more computer programs, which may be stored in one or more of the memories in the controller 100. The computer program portions may be written at any high level language such as C, C+, C++, or the like, or any low-level, assembly or machine language. By storing the computer program portions therein, various portions of the memories are physically and/or structurally configured in accordance with the computer program instructions.

Figure 3:
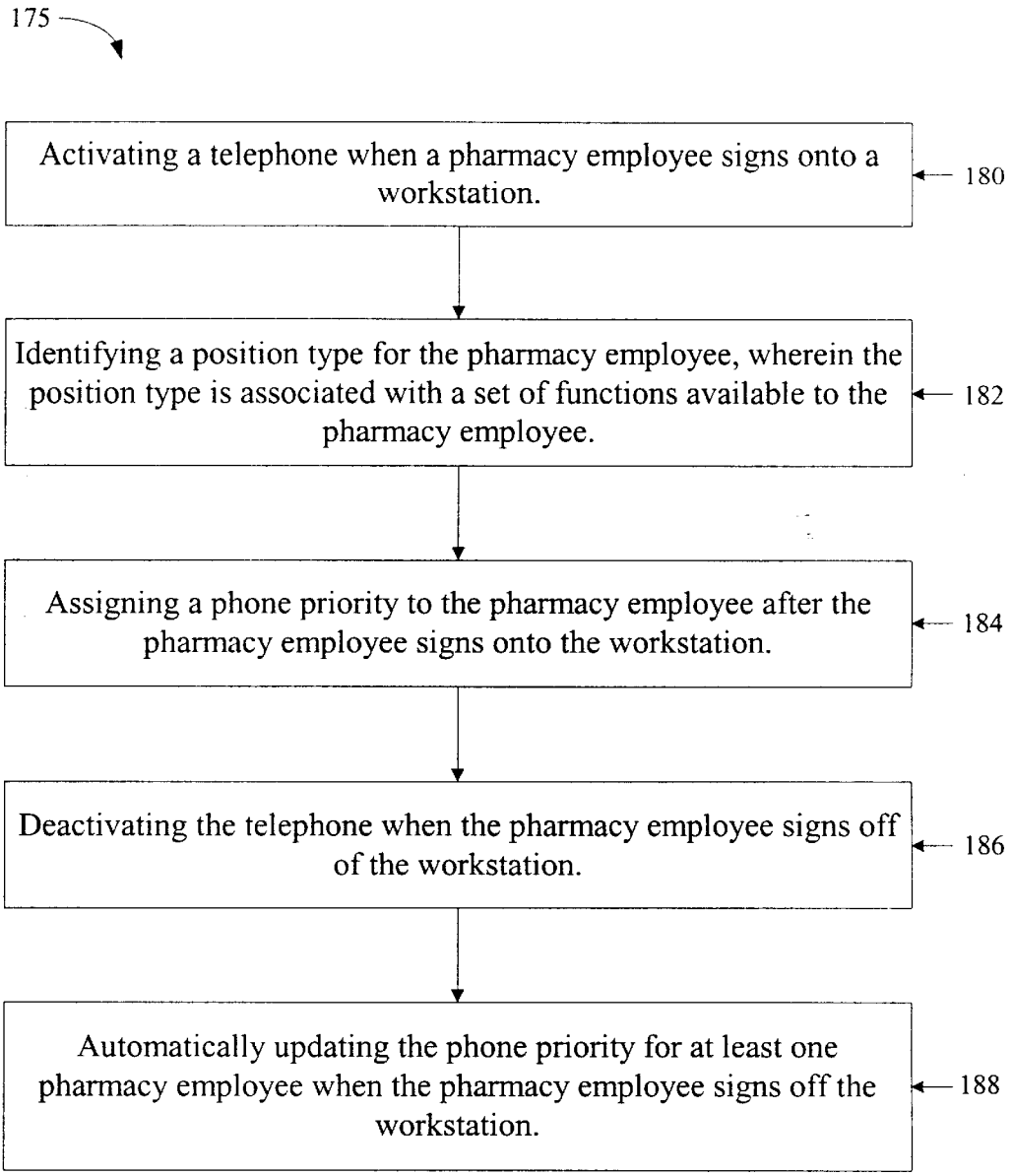
FIG. 3 is a flowchart of some of the steps used in assigning phone priorities for an automatic telephone routing system in accordance with an embodiment of the invention.

FIG. 3 illustrates some of the steps of an operating routine or subroutine 175 that may be stored in the memory of the controller 100. The routine 175 may be performed in preparation of the pharmacy receiving telephone calls from customers and may continue running during normal operating hours of the pharmacy. The routine 175 may begin operation at a block 180 during which a telephone is activated when a pharmacy employee signs onto a workstation. The sign on process may include entering a user name and a password associated with the pharmacy employee.

The system may then identify a position type of the pharmacy employee at a block 182, wherein the position type is associated with the set of functions available to the pharmacy employee. For example, the system may perform a lookup in a database and determine that the pharmacy employee signing onto the workstation is a registered pharmacist. The pharmacy may operate most efficiently if it is able to direct the majority of calls from prescribers to registered pharmacists that have signed onto workstations in the pharmacy. Thus, it may be important to know which workstations in the pharmacy have pharmacists signed onto those workstations.

After identifying the position type of the pharmacy employee at the block 182, the system may assign a phone priority to the pharmacy employee at a block 184. The phone priority may be the priority in which the phones will be routed. In other words, the phone priority may determine how the telephone calls are routed within the pharmacy. For example, if no pharmacists have signed onto the system, then the first pharmacist signing onto the system may be assigned a priority of "1." The next pharmacist signing onto the system may then automatically be assigned the next highest priority, or a priority "2." In this example, a first telephone call coming into the pharmacy from a prescriber may be directed to a pharmacist having the priority "1," unless, that pharmacist is currently on the telephone and thus unavailable, wherein the telephone call would then be directed to the pharmacist having the priority "2." If both pharmacists were unavailable, then the caller would be placed on hold, until one of the pharmacists becomes available. This will be described in more detail with reference to FIGS. 4A and 4B.

The phone priorities assigned to pharmacy employees may be manually modified to increase or decrease one or more phone priorities that have been automatically assigned, as well as removing the automatically assigned priority entirely to indicate that no calls should be directed to that pharmacy employee. The manual increase and/or manual decrease of phone priorities may thus result in altering the routing of telephone calls within the pharmacy. The system may also be flexible enough to allow pharmacy employees to sign onto telephones that are not associated with a workstation (i.e., a phone on a wall, a counter, etc.). Also, employees may sign onto a plurality of workstations, thus activating a plurality of telephones within the pharmacy. Further, employees may sign off of a work station for a variety of reasons, such as when completing a shift or when taking a break.

The system may deactivate the telephone after the pharmacy employee signs off the workstation, as shown at a block 186. At a block 188, the system may then automatically update the phone priority for at least one pharmacy employee after the pharmacy employee signs off of the workstation. For example, if a pharmacist having the highest phone priority signs off of a workstation, then all other pharmacists signed on to workstations will have their phone priorities reassigned. Thus, a pharmacist having a phone priority "2" would then be reassigned a phone priority "1." Pharmacy employees signing off of a workstation may have their phone priority removed, unless they are the only priority available, in which case, their priority may remain active. For example, if a pharmacy had only one pharmacist signed onto the system (phone priority "1"), and that pharmacist signed off of the system and left for the night, the system may be programmed to automatically update the pharmacist's priority, but would keep it as priority "1" because no other pharmacists were signed onto a workstation in the system. By requiring the pharmacy employees to sign on and off of workstations, the automatic telephone routing system automatically knows the number of pharmacy employees currently staffed, their position types, and locations within the pharmacy without having to worry about employee breaks, lunches, and other personnel changes that would normally require continuous manual updating in prior art systems.

Figure 4A:
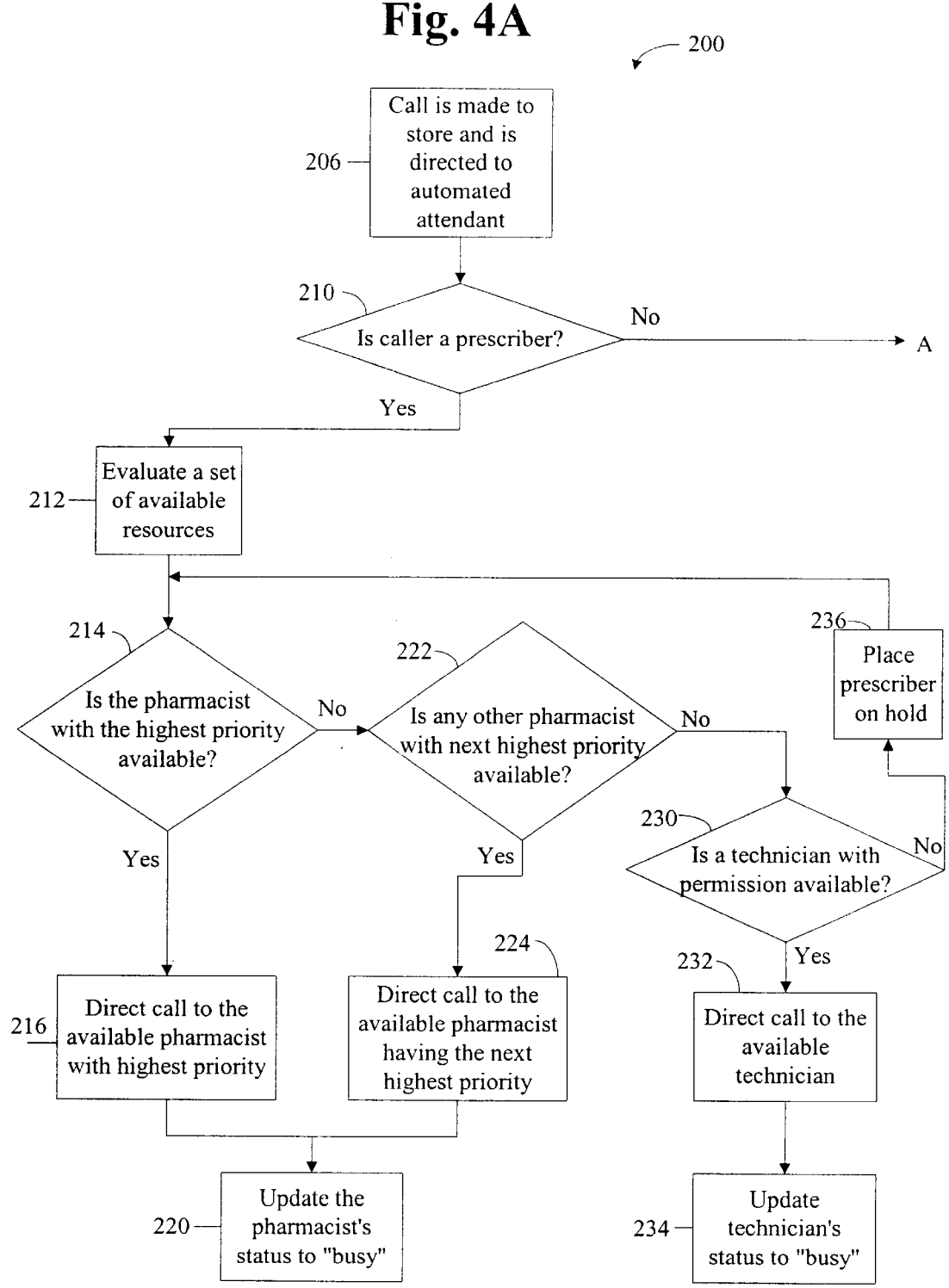
FIGS. 4A and 4B are two parts of a flowchart of an embodiment of a main routine that may be performed during operation of an automatic telephone routing system.
Figure 4B:
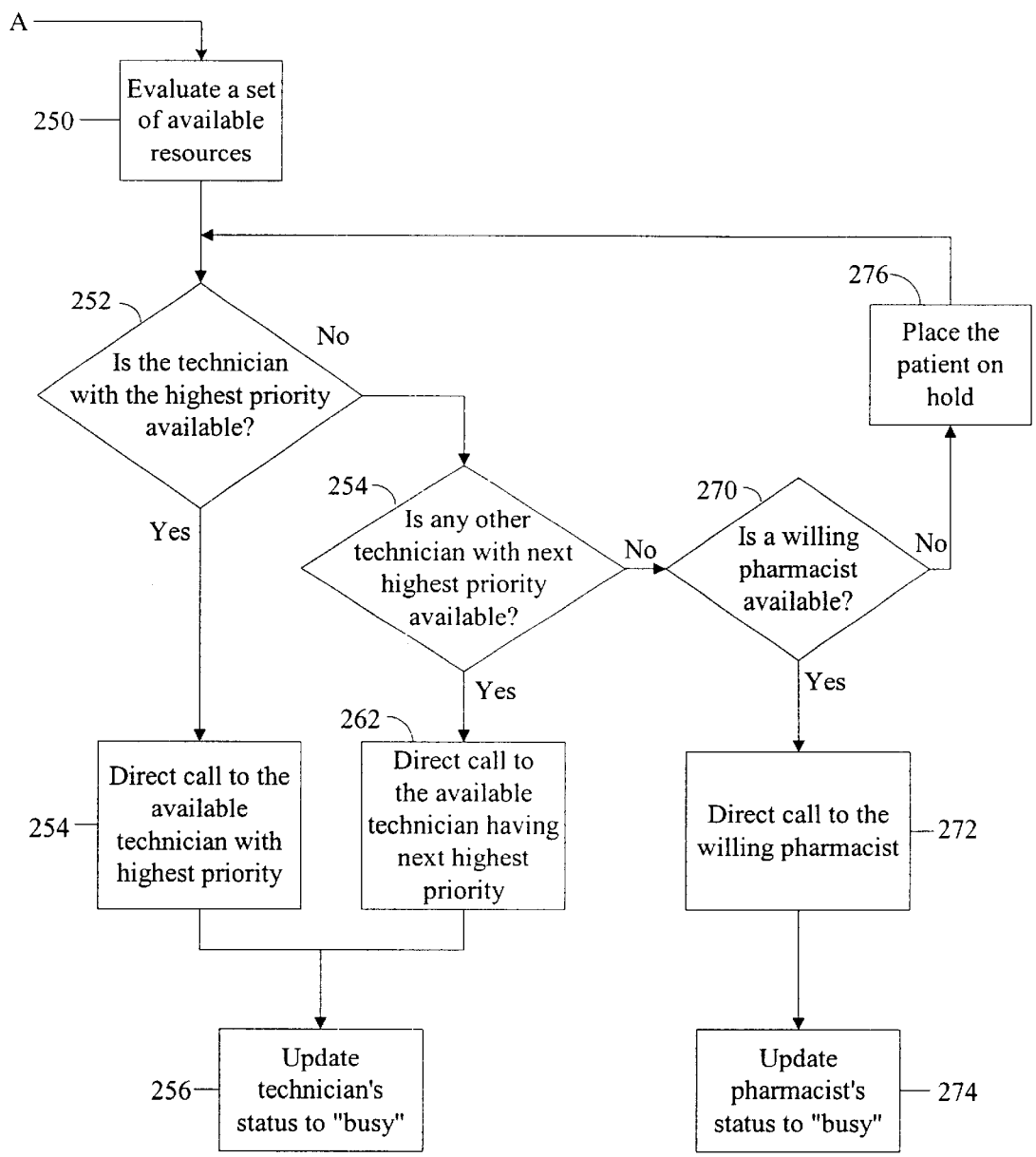

FIGS. 4A and 4B are two parts of a flow chart of a main operating routine 200 that may be stored in the memory of the controller 100. The main routine 200 may be utilized for automatic telephone routing systems that are designed to channel customers to the appropriate technicians and to channel prescribers to the appropriate pharmacist, in order to maximize the internal efficiency of the pharmacy portion of the store 20. Referring to FIG. 4A, the main routine 200 may begin operation when a customer calls a store and is directed to an automated attendant that is connected to a telephone switch, as shown at a block 202. For the purpose of this description, the term "customer" is intended to include all callers to the pharmacy, for example, patients, physicians, nurses, physician assistants, insurers, etc.

The automated attendant is used to identify the type of phone call associated with the caller. If it is determined at a block 210 that the customer is a prescriber, or someone from a prescriber's office, such as a nurse or a physician's assistant, then the system may evaluate a set of resources to handle the type of phone call at a block 212. The set of available resources in this case may include pharmacists that have signed onto a workstation. The set of available resources may also include technicians or other pharmacy employees that have been given permission to receive calls from prescribers, however these pharmacy employees are not automatically assigned backup responsibilities, but are required to manually modify the set of resources so that they are included in the set of resources.

If it is determined at a block 214 that the pharmacist with the highest priority ("1") is available (i.e., present, signed on, and not already on the telephone), then the system may direct the caller to the available pharmacy employee having the position type preferred to handle the call type and having the highest phone priority at the block 216. In other words, because the telephone call is from a prescriber or someone affiliated with the prescriber, then the telephone call is directed to the available pharmacist that has the highest phone priority. For example, if a pharmacy has two pharmacists that have signed onto workstations and neither pharmacist currently is occupied with a telephone call, then the next calling prescriber may be directed to the first pharmacist having the highest priority. Once the call is directed to the first pharmacist, then the system may update the pharmacist status to "busy" as shown at the block 220. If a second prescriber calls the pharmacy while the first pharmacist is still on the telephone and has a status set at "busy," then the system may check at a block 222 to see if another pharmacist with the next highest phone priority is signed onto the system and is available. This step may be repeated in a looping fashion to check a plurality of pharmacists to find the first one available that has the next highest phone priority. If the pharmacist with the next highest phone priority is available, then the system may direct the second caller to the available pharmacist having the next highest phone priority at a block 224. After directing a caller to the available pharmacist at the block 224, the system may update the pharmacist status to "busy" at the block 220.

If the system determines at the block 222 that no pharmacists are available to handle the telephone call, then the system may check at a block 230 if a technician is signed onto the system that has been given permission to handle prescriber calls. A technician may be given permission to handle prescriber calls in situations where, for example, the pharmacy currently does not have a pharmacist signed onto a work station, or where the pharmacists signed onto workstations are understaffed in relation to the anticipated volume of business at the pharmacy. The permission to manually override the system would only be given in locations where this step would not be in violation of state laws. In these situations, the system may direct the call to the available technician as shown at a block 232. The system may then update the technician's status to "busy" at a block 234.

After determining at the block 230 that a technician is not available and has not been given permission to handle prescriber calls, the system may place the prescriber on hold or in a hierarchical holding cue until a pharmacy employee from the set of resources capable of handling the telephone call becomes available, as shown at a block 236. The system may then return to the block 214 to continue checking for an available pharmacy employee. If multiple callers are placed on hold simultaneously, then the system may direct the caller that waited the longest on hold to the first available pharmacy employee. This method is sometimes referred to as "first in first out" or FIFO.

FIG. 4B is a second half of the flow chart of the main operating routine 200. After it is determined at the block 210 that the telephone call is not from a prescriber, (i.e., a patient, an insurer, etc.) the system may evaluate a set of resources at a block 250 that are available or capable of handling the type of telephone call. The set of resources may comprise one or more pharmacy employees that have each signed onto a work station. If it is determined at a block 252 that the technician with the highest phone priority is signed onto a work station and available, then the system may direct the patient or other caller to the available technician having the highest priority as shown at a block 254. After directing the telephone call to the technician with the highest phone priority at the block 254, the system may be updated to set the technician's status to "busy" at a block 256, check at a block 254 to see if there are multiple technicians available.

If it is determined at the block 252 that the technician with the highest priority was unavailable, then the system may check at a block 260 for another technician with the next highest phone priority is signed on and available. If another technician with the next highest priority is available, the system may direct the caller to the available technician at a block 262. In other words, the system may direct the caller to the pharmacy employee that is capable of handling that type of call, that is signed onto a workstation, and is not currently on the telephone with another customer. After directing the call to the available technician at the block 262, the system may then update the technician status to "busy" at the block 256.

The system may determine at the block 260 that a technician is not available to handle the telephone call, wherein the system may check at a block 270 to see if a pharmacist is available that is signed onto a workstation and has agreed to take patient or miscellaneous calls as a backup. The system may not automatically establish pharmacists as backups for technicians, but it may be necessary to manually arrange for the pharmacists to serve as backups for the technicians in some situations, such as when the pharmacy has only one pharmacist and one technician signed onto workstations. In these situations, the call may be directed to the available pharmacist at a block 272 and the system may update the pharmacist's status to "busy" at a block 274.

If it is determined at the block 270 that the pharmacy does not have a pharmacist signed onto a workstation that has agreed to take patient calls, then the system may place the caller on hold or in a hierarchical holding cue, until a pharmacy employee from the set of resources capable of handling the telephone call becomes available, as shown at the block 276. After placing the caller on hold at the block 276, the system may return to the block 252 to continue checking for an available pharmacy employee. The system may keep the caller waiting on hold until a caller previously connected to a pharmacy employee hangs up, thus, freeing the pharmacy employee and making him or her available to accept the telephone call.

Figure 5:
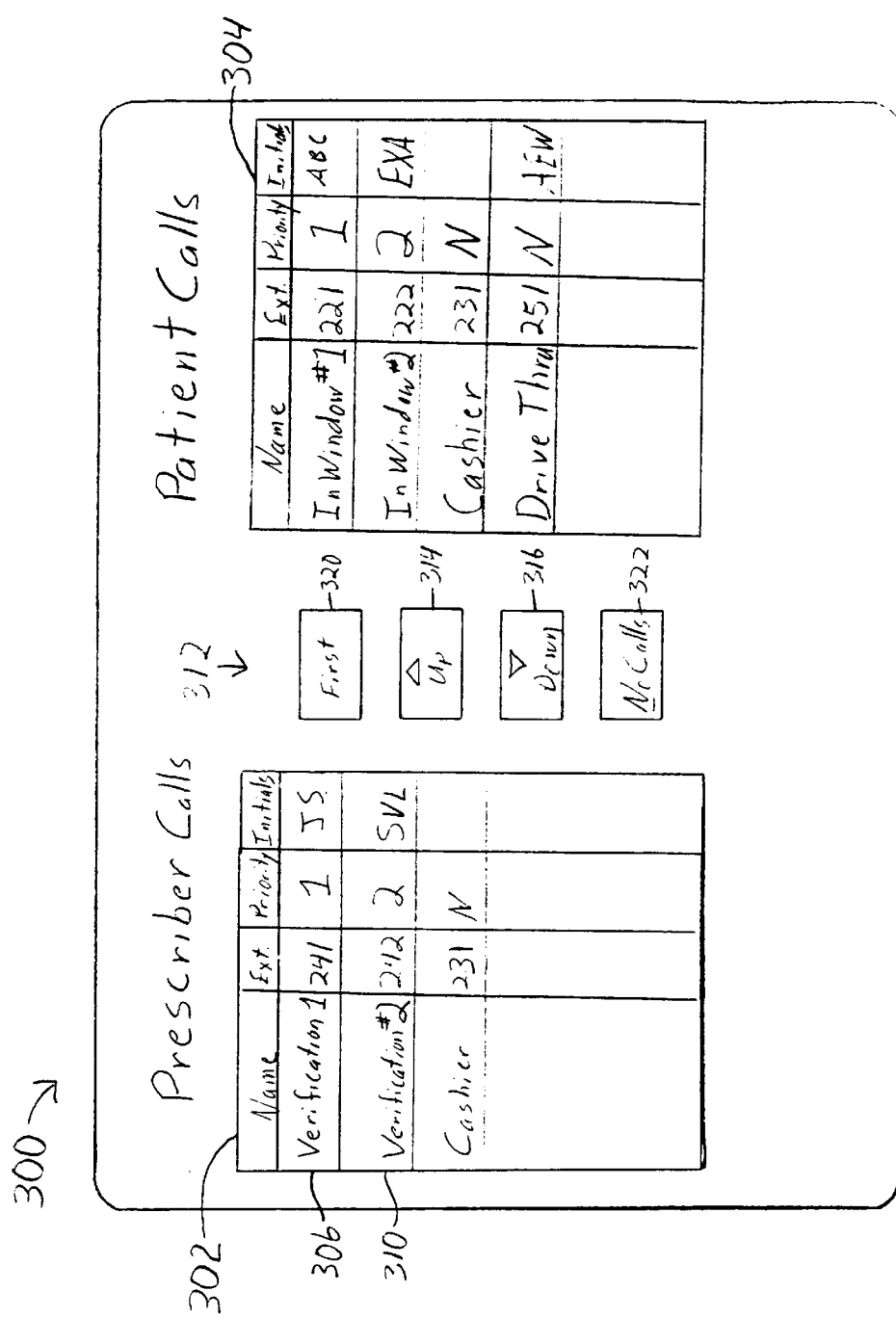
FIG. 5 is an exemplary graphic representation of a user interface in accordance with an embodiment of the invention.

Control of the automatic telephone routing system may be accomplished with the use of a user interface, such as the user interface 300 shown in FIG. 5. The user interface 300 may be split with a section 302 for prescriber calls on a left hand side of the user interface 300 and a section 304 for patient and other miscellaneous calls on a right hand side of the user interface 300. The sections 302 and 304 may display a variety of information, including the pharmacy employee's name, telephone extension, phone priority, and initials. The sections 302 and 304 may arrange the pharmacy employees in such a way that the employees having the highest phone priorities are listed nearest the top of the sections 302 and 304. A first entry 306 in the section 302 for prescriber calls identifies a pharmacist having the initials J.S., whose responsibilities include verification of prescriptions, and has a phone priority "1." The second entry 310 identifies another pharmacist having the initials S.V.L., with responsibilities for verification of prescriptions, and a listed phone priority "2." This visual depiction or graphical representation of the pharmacy employees signed onto workstations and their listed priorities assists in easily identifying the workflow and the method of routing telephone calls within the pharmacy.

The user interface 300 may also include a section 312 to manually adjust and override the phone priorities of the pharmacy employees identified in the sections 302 and 304. The section 312 may include an up button 314 and a down button 316 which may be utilized to increase or decrease a pharmacy employee's phone priority. The section 312 may also include a button 320 that may be utilized to manually move any entry for a pharmacy employee identified in the sections 302 and 304 to the top entry representing the first or highest priority. The first button 320 accomplishes what the up button 314 could also accomplish with repeated pushes of the up button 314. The section 312 may also include a no calls button 322 which may be used to designate a pharmacy employee as not receiving telephone calls. The user interface 300 thus provides a graphical depiction of the proposed routing or workflow of telephone calls within the pharmacy. The particular arrangement of the sections and buttons of the user interface 300 is not particular to the invention, and it should be appreciated that numerous adaptions may be created.

Although the technique for automatically routing telephone calls in a pharmacy as described herein is preferably implemented in software, it may be implemented in hardware, firmware, etc., and may be implemented by any other processor associated with the store. Thus, the routines described herein may be implemented in a standard multipurpose CPU or on specifically designed hardware or firmware as desired. When implemented in software, the software routine may be stored in any computer readable memory such as on a magnetic disk, a laser disk, or other storage medium, in a RAM or ROM of a computer or processor, etc. Likewise, the software may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

The invention has been described in terms of several preferred embodiments. It will be appreciated that the invention may otherwise be embodied without departing from the fair scope of the invention defined by the following claims.

We claim:

1. A method of automatically routing a telephone call in a pharmacy, comprising the steps of:

activating a telephone when a pharmacy employee signs onto a workstation;

identifying a position type for the pharmacy employee, wherein the position type is associated with a set of functions available to the pharmacy employee;

assigning a phone priority to the pharmacy employee after the pharmacy employee signs onto the workstation;

identifying a type of caller associated with the telephone call, the type of caller selected from the group consisting of a prescriber, a person associated with a prescriber, a patient, and an insurer;

evaluating a set of resources available to handle the type of caller;

directing the caller to an available pharmacy employee having the position type preferred to handle the type of caller and having the highest phone priority;

placing the caller in a hierarchical holding cue if no pharmacy employee having the position preferred to handle the type of caller is available until a pharmacy employee having the position type preferred to handle the type of caller becomes available; and deactivating the telephone when the pharmacy employee signs off of the workstation.

2. The method of claim 1, wherein the step of activating the telephone when the pharmacy employee signs onto the workstation is repeated to allow the pharmacy employee to sign onto a plurality of workstations, thus activating a plurality of telephones.

3. The method of claim 1, further comprising the step of allowing a manual increase or a manual decrease of the phone priority assigned to the pharmacy employee.

4. The method of claim 1, wherein the position type is selected from the group of position types consisting of pharmacists and technicians.

5. The method of claim 1, wherein the workstation comprises a controller, a display, a data input apparatus, and a telephone.

6. The method of claim 1, wherein the step of identifying the type of caller associated with the telephone call is performed with the use of an automated attendant.

7. The method of claim 1, further comprising the step of automatically updating the phone priority for at least one pharmacy employee when the pharmacy employee signs off of the workstation.

8. The method of claim 1, further comprising the step of automatically assigning another position type, that is associated with another set of functions available to the pharmacy employee, to the pharmacy employee when there is only one pharmacy employee of each position type signed onto the system.

9. A method of automatically routing a telephone call in a pharmacy, comprising the steps of:

activating a telephone when a pharmacy employee signs onto a workstation;

identifying whether the pharmacy employee is a pharmacist or a technician;

assigning a phone priority to the pharmacy employee after the pharmacy employee signs onto the workstation;

identifying whether the telephone call is from a prescriber or from a patient;

evaluating a set of resources capable of handling the telephone call, wherein the set of resources comprises one or more pharmacy employees that have each signed onto a workstation;

directing the telephone call to an available pharmacist if the telephone call is from a prescriber;

directing the telephone call to one of an available technician and an available pharmacist if the telephone call is from a patient;

placing the caller in a hierarchical holding cue if the set of resources capable of handling the telephone call does not have an available pharmacy employee, until a pharmacy employee from the set of resources capable of handling the telephone call becomes available; and deactivating the telephone when the pharmacy employee signs off of the workstation.

10. The method of claim 9, wherein the step of activating the telephone when the pharmacy employee signs onto the workstation may be repeated to allow the pharmacy employee to sign onto a plurality of workstations, thus activating a plurality of telephones.

11. The method of claim 9, further comprising the step of allowing a manual increase or a manual decrease of the phone priority assigned to the pharmacy employee.

12. The method of claim 9, wherein the workstation comprises a controller, a display, a data input apparatus, and a telephone.

13. The method of claim 9, wherein the step of identifying whether the telephone call is from a prescriber or from a patient is performed with the use of an automated attendant.

14. The method of claim 9, further comprising the step of automatically updating the phone priority for at least one pharmacy employee when the pharmacy employee signs off of the workstation.

15. The method of claim 9, wherein the step of directing the telephone call to one of an available technician and an available pharmacist if the telephone call is from a patient has a preferred order comprising first attempting to direct the telephone call to a technician if a technician is available, then directing the telephone call to a pharmacist if the set of resources capable of handling the call includes a pharmacist that has agreed to receive calls from patients.

16. A system for automatically routing a telephone call in a pharmacy for an organization having a processor, the system comprising:

a memory;

a first software routine stored in the memory and adapted to be executed on the processor to execute the step of activating a telephone when a pharmacy employee signs onto a workstation;

a second software routine stored in the memory and adapted to be executed on the processor to execute the step of identifying a position type for the pharmacy employee, wherein the position type is associated with a set of functions available to the pharmacy employee;

a third software routine stored in the memory and adapted to be executed on the processor to execute the step of assigning a phone priority to the pharmacy employee after the pharmacy employee signs onto the workstation;

a fourth software routine stored in the memory and adapted to be executed on the processor to execute the step of identifying a type of caller associated with the telephone call, the type of caller selected from the group consisting of a prescriber, a person associated with a prescriber, a patient, and an insurer;

a fifth software routine stored in the memory and adapted to be executed on the processor to execute the step of evaluating a set of resources available to handle the type of caller;

a sixth software routine stored in the memory and adapted to be executed on the processor to execute the step of directing the caller to an available pharmacy employee having the position type preferred to handle the type of caller and having the highest phone priority;

a seventh software routine stored in the memory and adapted to be executed on the processor to execute the step of placing the caller in a hierarchical holding cue if no pharmacy employee having the position preferred to handle the type of caller is available until a pharmacy employee having the position type preferred to handle the type of caller becomes available; and an eighth software routine stored in the memory and adapted to be executed on the processor to execute the step of deactivating the telephone when the pharmacy employee signs off of the workstation.

17. The system of claim 16, wherein the first software routine stored in the memory and adapted to be executed on the processor to execute the step of activating a telephone when a pharmacy employee signs onto a workstation is repeated to allow the pharmacy employee to sign onto a plurality of workstations, thus activating a plurality of telephones.

18. The system of claim 16, wherein the system further comprises a ninth software routine stored in the memory and adapted to be executed on the processor to execute the step of allowing a manual increase or a manual decrease of the phone priority assigned to the pharmacy employee.

19. The system of claim 16, wherein the second software routine stored in the memory and adapted to be executed on the processor is adapted to select the position type from the group of position types consisting of pharmacists and technicians.

20. The system of claim 16, wherein the fourth software routine stored in the memory and adapted to be executed on the processor is adapted to be performed with the assistance of an automated attendant.

21. The system of claim 16, further comprising a ninth software routine stored in the memory and adapted to be executed on the processor to execute the step of automatically updating the phone priority for at least one pharmacy employee when the pharmacy employee signs off of the workstation.

22. The system of claim 16, further comprising a ninth software routine stored in the memory and adapted to be executed on the processor to execute the step of automatically designating another position type, that is associated with another set of functions available to the pharmacy employee, to the pharmacy employee when there is only one pharmacy employee of each position type signed onto the system.

* * * * *

UNITED STATES PATENT AND TRADEMARK OFFICE
CERTIFICATE OF CORRECTION

PATENT NO. : 6,891,946 B2  Page 1 of 1
DATED : May 10, 2005
INVENTOR(S) : Dejan Kozic and Karl E. Meehan It is certified that error appears in the above-identified patent and that said Letters Patent is hereby corrected as shown below:

<u>Title page,</u>
Item [57], ABSTRACT,
Line 14, "cue" should be -- queue --

<u>Column 9,</u>
Line 15, "cue" should be -- queue --

<u>Column 10,</u>
Line 1, "cue" should be -- queue --

<u>Column 11,</u>
Line 3, "cue" should be -- queue --

Signed and Sealed this

Second Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,891,946 B2  
DATED : May 10, 2005  
INVENTOR(S) : Dejan Kozic et al.

It is certified that error appears in the above-identified patent and that said Letters Patent is hereby corrected as shown below:

Title page,
Item [73], Assignee, please delete "Walgreen, Co.," and insert -- Walgreen Co., --.

Column 8,
Line 67, please delete "workstation;" and insert -- workstation, thereby allowing said employee to activate a plurality of telephones by signing onto a plurality of workstations; --.

Column 9,
Line 52, please delete "workstation;" and insert -- workstation, thereby allowing said employee to activate a plurality of telephones by signing onto a plurality of workstations; --.

Column 10,
Line 41, please delete "workstation;" and insert -- workstation, thereby allowing said employee to activate a plurality of telephones by signing onto a plurality of workstations; --.

Signed and Sealed this

Eleventh Day of October, 2005

JON W. DUDAS
*Director of the United States Patent and Trademark Office*